US009883836B2

(12) United States Patent
Cahan et al.

(10) Patent No.: US 9,883,836 B2
(45) Date of Patent: Feb. 6, 2018

(54) EMBEDDED DEVICE FOR FLOW MONITORING

(71) Applicant: International Business Machines Corporation, Armonk, NY (US)

(72) Inventors: Amos Cahan, Dobbs Ferry, NY (US); Hariklia Deligianni, Alpine, NJ (US); Pei-Yun S. Hsueh, Hawthorne, NY (US); Theodore G. van Kessel, Millbrook, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 15/018,218

(22) Filed: Feb. 8, 2016

(65) Prior Publication Data

US 2017/0224279 A1  Aug. 10, 2017

(51) Int. Cl.
   *A61B 8/14* (2006.01)
   *A61B 5/00* (2006.01)
   (Continued)

(52) U.S. Cl.
   CPC ............ *A61B 5/686* (2013.01); *A61B 5/0402* (2013.01); *A61B 5/076* (2013.01); *A61B 7/045* (2013.01);
   (Continued)

(58) Field of Classification Search
   CPC ........................................................ A61F 2/24
   See application file for complete search history.

(56) References Cited

U.S. PATENT DOCUMENTS 5,289,821 A   3/1994 Swartz
6,251,061 B1* 6/2001 Hastings ............. A61M 1/1068
                                                600/16
(Continued)

OTHER PUBLICATIONS

"Energy Harvesting from the Cardiovascular System, or How to Get a Little Help from Yourself" by A. Pfenniger et al. Annals of Biomedical Engineering, vol. 40, No. 11, Nov. 2013, pp. 2248-2263.*

(Continued)

*Primary Examiner* — Tse Chen
*Assistant Examiner* — Jason Ip
(74) *Attorney, Agent, or Firm* — Scully, Scott, Murphy & Presser, P.C.; Rabin Bhattacharya

(57) ABSTRACT

A system and method for monitoring a health status of a subject. The system comprises: a medical device implantable in the subject and having a passage or compartment through which blood flows through; a sensor device embedded at or near a surface of said passage within said medical device for generating signals suitable for measuring a Doppler shift effect occurring within said passage; and a control device coupled to said sensor device for measuring a liquid blood flow rate within said passage based on sensor generated signals outputs. The embedded sensor device comprises a first piezo-electric element configured to generate an acoustic excitation signal and a second piezo-electric element configured to receive said acoustic excitation signal. The second piezo-electric element emits a signal responsive to said acoustic excitation signal. Control device in real time compares a generated output signal with the input excitation signal to determine a Doppler frequency shift measurement.

20 Claims, 6 Drawing Sheets

(51) Int. Cl.

| | | |
|---|---|---|
| *A61F 2/82* | (2013.01) | |
| *A61F 2/07* | (2013.01) | |
| *A61F 2/24* | (2006.01) | |
| *A61B 8/06* | (2006.01) | |
| *A61B 8/08* | (2006.01) | |
| *A61B 5/07* | (2006.01) | |
| *A61B 8/04* | (2006.01) | |
| *A61B 8/02* | (2006.01) | |
| *A61B 5/0402* | (2006.01) | |
| *A61B 7/04* | (2006.01) | |

(52) U.S. Cl.
CPC .............. *A61B 8/02* (2013.01); *A61B 8/04* (2013.01); *A61B 8/06* (2013.01); *A61B 8/488* (2013.01); *A61B 8/5223* (2013.01); *A61F 2/07* (2013.01); *A61F 2/24* (2013.01); *A61F 2/82* (2013.01); *A61B 2562/0219* (2013.01)

(56) References Cited

U.S. PATENT DOCUMENTS

| | | | |
|---|---|---|---|
| 6,398,734 B1 * | 6/2002 | Cimochowski | A61B 8/0858 600/443 |
| 7,128,713 B2 | 10/2006 | Moehring et al. | |
| 7,494,459 B2 | 2/2009 | Anstadt et al. | |
| 7,925,329 B2 | 4/2011 | Zdeblick et al. | |
| 8,298,148 B2 | 10/2012 | Furman | |
| 2005/0121734 A1 * | 6/2005 | Degertekin | A61B 5/0215 257/414 |
| 2006/0129050 A1 * | 6/2006 | Martinson | A61B 5/07 600/505 |
| 2013/0303916 A1 * | 11/2013 | Aoki | A61B 8/065 600/454 |
| 2014/0336474 A1 * | 11/2014 | Arbabian | H04B 11/00 600/301 |

OTHER PUBLICATIONS

Bazan, et al., "A new high-resolution spectral approach to noninvasively evaluate wall deformation in arteries" Computational and Mathematical Methods in Medicine, Jan. 1, 2014, 14 pages.

Latifoglu, et al., "Medical diagnosis of atherosclerosis from carotid artery doppler signals using principle component analysis (pca), k-nn based weighting pre-processing and artificial immune recognition system (AIRS)", Journal of Biomedical Informatics 41, 2008, pp. 15-23.

* cited by examiner

EMBEDDED DEVICE FOR FLOW MONITORING

FIELD

The present disclosure relates to the field of flow monitoring, such as liquid flow monitoring, and more particularly to a system and method for monitoring blood flow in the body of an individual through an implantable device, the device being a vascular stent or graft, a prosthetic cardiac valve or an artificial heart.

BACKGROUND

Currently, in the medical field, as it pertains to pulmonary and/or circulatory system diseases in animals, stents (such as in coronary arteries) and grafts (such as used in the Aorta) provide an important treatment modality used both to treat narrowing or occlusion of the arterial lumen (e.g., in coronary artery disease or renal artery stenosis) as well as for widening of the lumen because of a disease in the vessel wall (e.g., an aortic aneurysm). Vascular stents are usually made of metal and vascular grafts are commonly made of Dacron.

Narrowing of the lumen of a stent or graft may follow implantation. This may be due to proliferation of tissue surrounding the stent or graft (restenosis). Narrowing of the lumen of a stent or graft may also be due to the formation of a blood clot on the surface of a stent or graft facing the vessel lumen (e.g. in-stent thrombosis). Patients with a coronary artery stent are usually prescribed medications to prevent blood clot formation on the stent. Narrowing of the lumen of a stent or graft may further be caused by an embolus from another part of the body that cannot pass through a stent or graft, said embolus be composed of a blood clot, microorganisms, or fat.

Noninvasive measurement of blood flow across an intravascular device is inaccurate and requires special equipment and expertise which are not readily available. Occlusion of a coronary artery by in-stent thrombosis may result in sudden cardiac death from a myocardial infarction (heart attack) or a fatal arrhythmia. Occlusion of a stent elsewhere can cause ischemia and infarction of tissues supplied by the vessel in which the stent had been implanted.

Moreover, the gold standard methods for cardiac output measurement are invasive, complicated and risky.

It is the case that non-invasive assessment using external ultrasound-Doppler devices is less accurate.

However, cardiac output measurement is key to diagnosing and treating both acute and chronic conditions. For example, it is clinically important and useful to know whether a patient presenting with shortness of breath suffers from a primary respiratory pulmonary disease or from a heart problem.

Cardiac output may change in the presence of volume overload, pressure overload and ischemia. Changes in cardiac output may precede the clinical manifestations of diseases. For example, reduced cardiac output may precede the development of pulmonary edema. Early cardiac ischemia may cause impaired relaxation of the ventricular wall, leading to decreased cardiac output even before acute ischemia (e.g. myocardial infarction) is present. A cardiac arrhythmia may be asymptomatic but lead to decreased cardiac output. For example, atrial fibrillation, a common arrhythmia that may go unnoticed by a patient reduces cardiac output by eliminating the "atrial kick" that actively pumps blood into the ventricle.

Furthermore, failure of a prosthetic valve may be the result of prolonged wear and tear but may also indicate a dangerous but potentially curable condition like stuck valve (the formation of a blood clot on the valve compromising leaf movement) or infection or inflammation causing vegetation formation on the valve.

Changes in the flow across a prosthetic heart valve may also be the result of leakage around the valve (paravalvular leak). These conditions may be insidious and thus diagnosis may be delayed, or they could be abrupt, resulting in a medical emergency.

Assessment of a valve function is most commonly done using echocardiography, which requires special equipment and professional operation, and thus is not readily available on demand.

Artificial hearts are used when a patient's native heart has failed either temporarily (e.g. during the course of myocarditis or acute ischemia) or permanently (e.g. due to dilated cardiomyopathy). Various designs have been developed, propelling blood in addition to or instead of one or more compartments of the heart. These devices have high energy consumption and are prone to blood clot formation or infection that may reduce their function.

SUMMARY

A system, method and computer program product for automatically monitoring blood flow across stents or grafts in the body of an individual in a continuous, noninvasive manner.

In one aspect, blood flow is monitored through an implantable device, said device being a vascular stent or graft, a prosthetic cardiac valve or an artificial heart. By monitoring blood flow through an implantable device, information about the health status of the patient who has the device implanted in their body as well as the function of said device can be inferred.

In some embodiments, flow monitoring enables measurement of cardiac output.

In accordance with one aspect, there is provided a system for monitoring a health status of a subject. The system comprises: a medical device implantable in the subject and having a passage or compartment through which blood flows through; a sensor device embedded at or near a surface of the passage within the medical device for generating signals suitable for measuring a Doppler shift effect occurring within the passage; and a control device coupled to the sensor device for measuring a liquid blood flow rate within the passage based on sensor generated output signals.

In another embodiment, there is provided a method for monitoring a health status of a subject. The method comprises: implanting a medical device in the subject at a passage or compartment through which blood flows through, the medical device having a sensor device embedded at or near a surface of the passage; generating signals, by the embedded sensor device, the signals suitable for measuring a Doppler shift effect occurring within the passage or compartment; communicating the generated signals to a processor device; and determining at the processor device, a liquid blood flow rate measure within the passage based on the received sensor generated signals.

In a further aspect, there is provided a computer program product for performing operations. The computer program product includes a storage medium readable by a processing circuit and storing instructions run by the processing circuit for running a method. The method is the same as listed above.

BRIEF DESCRIPTION OF THE DRAWINGS

Various objects, features and advantages of the present invention will become apparent to one skilled in the art, in view of the following detailed description taken in combination with the attached drawings, in which.

DETAILED DESCRIPTION

The disclosure presents a system and method for monitoring blood flow in the body of an individual. In one aspect, blood flow may be monitored across stents or grafts in a continuous, noninvasive manner.

Further, the disclosure presents a system and method for continuous, automatic monitoring of cardiac output, including at home and especially in patients with heart disease to guide early diagnosis and effective treatment for their conditions.

Further, the disclosure presents a system and method for obtaining real time information on the function of prosthetic valves to allow for early diagnosis of conditions affecting valvular function, where delayed diagnosis may have grave clinical consequences. For example, being able to monitor the function of artificial heart devices may allow for more efficient use of energy, enable early detection of malfunction and support.

More specifically, the disclosure relates to monitoring blood flow through an implantable device, the device being a vascular stent or graft, a prosthetic cardiac valve, an artificial heart vascular stent or graft, a venous filter, a prosthetic heart valve, an artificial heart or a bone implant. By monitoring blood flow through an implantable device, information about the health status of the patient who has the device implanted in their body as well as the function of the device can be inferred. In some embodiments, flow monitoring enables measurement of cardiac output.

In one embodiment, the systems and methods describe herein enable the estimation of the flow across a portion of a blood vessel or a compartment of the heart using an ultrasound Doppler transmission sensor.

In one embodiment, the system performs an operator-independent, automatic intermittent or continuous monitoring of flow through a miniaturized Doppler transmitter-sensor embedded within implantable medical devices such as including, but not limited to: vascular stents/grafts, venous filters, prosthetic heart valves, artificial hearts or bone implants. The Doppler device can monitor blood flow across the implant in which it is embedded and detect changes in flow that are the result of decreased systemic blood flow or a process comprising the function of the implant such as blood clotting, infection, inflammation or tissue proliferation leading to restenosis of the lumen. In the case of prosthetic heart valves, or aortic grafts, cardiac output can be accurately measured continuously.

Figure 1:
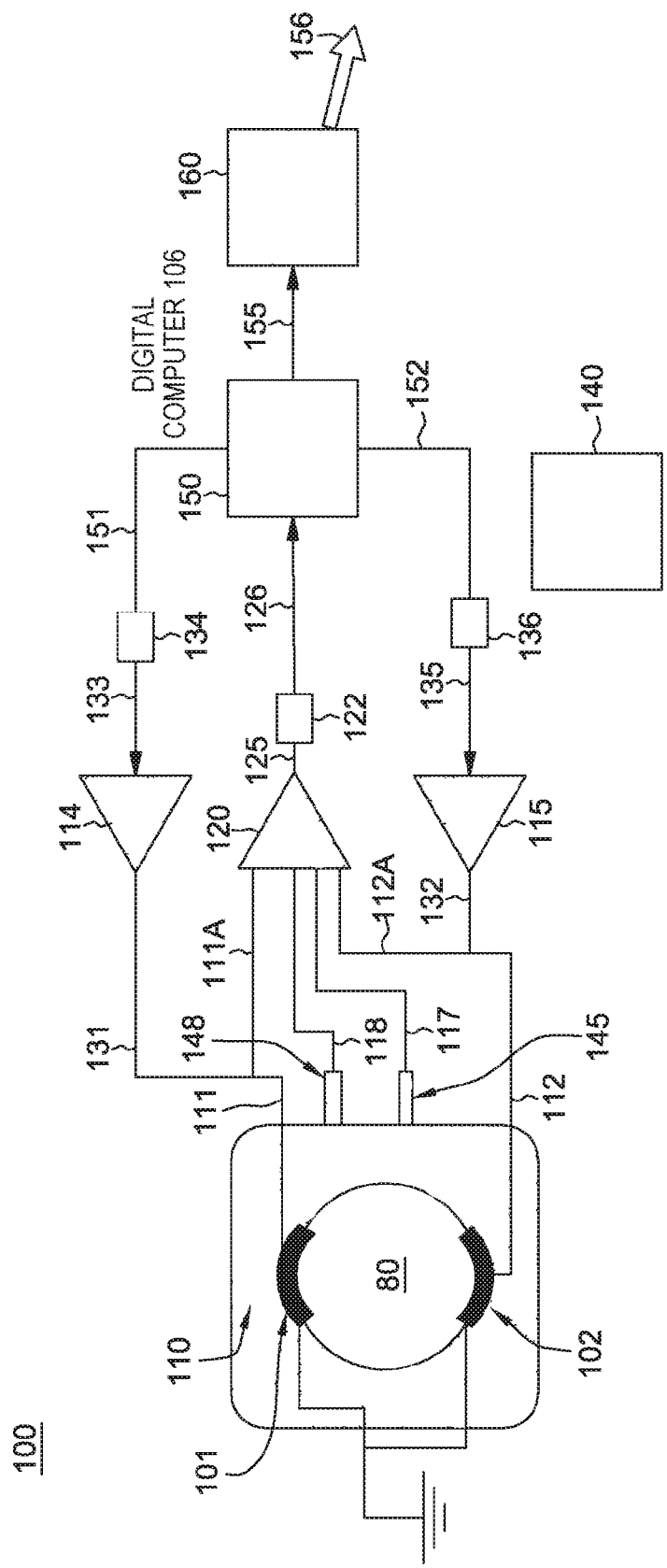
FIG. 1 illustrates a basic embodiment of an ultrasonic flow detection sensor system in one embodiment.

FIG. 1 illustrates the basic elements of the flow sensor and fluid flow monitoring system 100 that may be wholly implanted internally within a human. The monitoring system 100 includes a small sized implantable medical device 110 such as a heart valve, an arterial stent device, or like device having a passage within which blood or bodily fluid flows. Such a device, i.e., valve, stent, etc. forms a cavity or compartment 80 in which fluid, e.g., blood, flows, such as in an artery, or as a heart valve. On inner surfaces of the compartment in which the fluid flows is formed a miniaturized Doppler transmitter-sensor having formed piezo-electric elements 101, 102 respectively. In the embodiments described herein, piezo-electric elements are sensors the measure changes in a frequency signal using a Doppler effect operating in the ultrasonic range frequencies and generate a voltage in response to the applied stress.

In one embodiment, the flow monitoring system 100 is embodied as an integrated circuit or "biochip" module embedded in the implantable stent or mitral valve device in a subject. The biochip can be configured to act as an independent or interdependent biochip. As an independent or "stand-alone" unit, the biochip functions independently and has integrated function and/or communication with one or more sources external to the subject, e.g., a host monitoring system. As an interdependent or "systemic" unit, the biochip may further or communicate, e.g., via IEEE 802.x protocol, in tandem with one or more additional biochips within the subject. Interdependent biochips can have integrated function and/or communications with one or more sources external to the subject, alternatively or in addition to biochip inter-functionality.

As shown in FIG. 1, in one non-limiting embodiment, piezo-electric elements 101, 102 are located at opposite surfaces of the compartment 80, for example, with a second piezo-electric element located slightly downstream from the first piezo-electric element. Each piezo electric element 101, 102 includes two terminals, a ground terminal and an input or output (I/O) terminal. One terminal of each piezo-electric element 101, 102 is shown connected to a ground while the I/O terminals are each in respective electrical connection with respective conductors 111, 112, which carry voltage signals to and from respective piezo-electric elements 101, 102. For example, one piezo-electric may receive an applied stimulus via its I/O terminal while the second piezo-electric element may generate a signal responsive to an applied stimulus for output via its I/O terminal. In one embodiment, each to respective conductors 111, 112 conducts a respective output signal from a piezo-element to a respective conductive input 111A, 112A of a multichannel amplifier 120 which can detect and amplify a frequency signal output of the respective piezo-electric element 101, 102. Further, the analog input signals 131, 132 conducted to excite the piezo-electric elements 101, 102 may be further connected to respective input 111A, 112A of a multichannel amplifier 120 which can detect and amplify a frequency signal input to the respective piezo-electric element 101, 102. The amplified output voltage signal(s) 125 of a piezo-electric sensor element 101, 102 may be further input to an analog-todigital (A/D) converter element 122 to convert sensor output signal into a multi-bit digital data signal 126 which may be buffered/stored in a memory storage element and/or directly communicated for input to a register for direct use by a digitally programmed processing element such as a microcontroller, a microprocessor or like control device 150 ("controller") for local processing in determining a state of a bodily structure or organ based on the sensor data received. For example, the local processing may include determining at the controller, a magnitude of the blood flow (velocity), determining the duration of the flow and the shape of the flow curve, e.g., a short burst versus a more extended flow, determining whether the flow stops, and determining whether the flow is in the correct direction (e.g., not a leaky valve).

Figure 6:
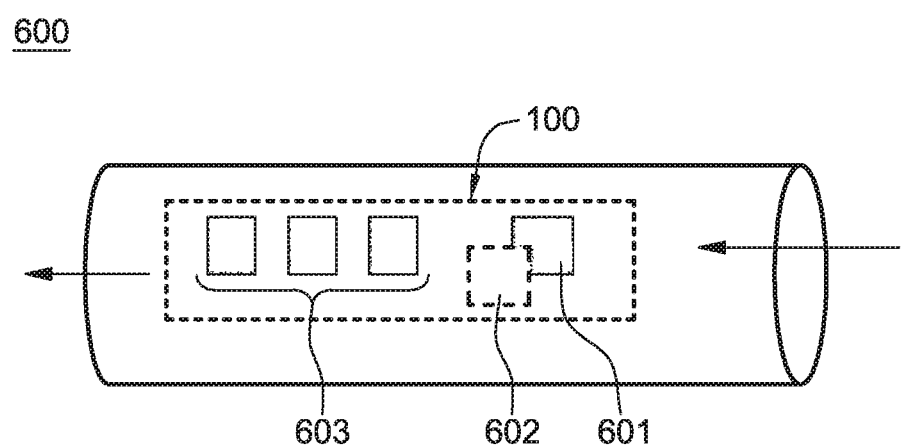
FIG. 6 depicts an alternate embodiment of a flow monitoring system including multiple receiver piezo-electric elements, e.g., in a phased-array configuration.

In alternate embodiments, system 100 may include two or more piezo-electric elements than shown in the embodiment of FIG. 1. For example, there may be multiple piezo-electric elements, e.g., in a phased-array configuration, with one piezo-electric element being excited to emit and remaining multiple of piezo-electric elements receiving the emitted signal. Thus, more information may be received from the multiple excited piezo-electric receiver elements of the array. For example, as shown in FIG. 6, an example stent device 600 may include a flow monitoring system 100 wherein embedded in the implanted device on one side of a passage or compartment surface is one transmitting piezo-element 601 that may be emit an ultrasonic signal in the direction of blood flow indicated by the arrows, for receipt by a receiving piezo-element 602 at the opposing passage or compartment surface directly in front or diagonal from the emitting element 601, and further for receipt at further piezo-elements 603 located on the same surface further down stream of the emitting element 601 and receiving element 602. In this embodiment, piezo-elements 602,603 are stimulated to provide additional information that is captured at respective channels of multichannel amplifier 120 and conveyed from the receiver piezo-elements to the controller for use pinpointing a particular issue, and/or separate out important variables.

In one embodiment, controller device 150 may generate a data output signal 155 which may include the digitized raw sensor data output signal, or computed flow rate output signal, or an output such as an alarm signal indicating a particular status of a bodily organ, for example, as would be determined by controller 150. The output signal 155 may be conducted via a conductor to a transmitter or transponder device 160 that may operate in accordance with a Wi-Fi standard, Bluetooth, ultrasound, or RFID communications standard. The transmitter device 160 may be located in vivo (within the implanted device), and provided to communicate collected information to an ex vivo receiver/transmitter device (such as on a patch on the patient's skin), e.g., via wired or wireless digital data signals 156.

Such a controller or microprocessor-based device 150 may further operate as an ultrasonic frequency signal generator (not shown) that may be programmed to generate a respective digital signal 151, 152 representing a stimulus ultrasonic frequency signal which may be input to a respective piezo-element 101, 102 as an ultrasonic or acoustic frequency signal, e.g., 25 kHz to 1.5 MHz. In one embodiment, digital signals 151 representing an acoustic frequency or ultrasonic frequency signal (a sound wave including a humanly inaudible sound) may be generated by controller element 150 and directly input to an digital-to-analog (D/A) converter element 134 to convert the digital signal 152 into a respective analog signal 133. Analog acoustic frequency or ultrasonic frequency 133 may be directly amplified by amplifier 114 to provide analog signal stimulus at piezo-electric element 101 in the form of respective amplifier output signal 131. Similarly, digital signals 152 representing an acoustic frequency or ultrasonic frequency signal may be generated by controller element 150 and directly input to a digital-to-analog (D/A) converter element 136 to convert the digital signal 152 into a respective analog signal 135. Analog acoustic frequency or ultrasonic frequency 133 may be directly amplified by amplifier 115 to provide analog signal stimulus at piezo-electric element 102 in the form of respective amplifier output signal 131. In this embodiment, the acoustic frequency or ultrasonic frequency signals 131, 132 may be carried on a respective conductor 111, 112 for input as stimulus to the respective elements 101, 102.

In one embodiment, via the system 100, micro-controller device 150 may generate a respective digital signal 151, 152 of a specified voltage or frequency which is then D/A converted and applied to a respective multichannel amplifier 114, 115 for applying a respective impedance matching input drive signal 131, 132 to a respective small piezo-element 101, 102 embedded in the implantable device 110. Regarding signal waveform generation for driving piezo-element 101 at acoustic frequencies, the controller 150 may provide digital values at correct time intervals to the amplifier and D/A converter 136 to result in a desired waveform. Those skilled in the art will recognize that amplifier/D/A converters are available with buffering and sequencing to further facilitate the generation of continuous waveforms. In such an embodiment, the controller element 150 will load a finite sequence of values into a buffer and the amplifier/D/A converter system will automatically cycle through the sequence at a user selectable rate to generate a continuous waveform.

Driving piezo-element 101 vibrates it in response to the applied input drive signals from amplifier 114 thereby producing an ultrasonic acoustic signal. This signal traverses the lumen of a blood-filled compartment such as the opening of a cardiac valve and may be physically detected by the other piezo-element 102 which responsively emits an output voltage which is amplified and then digitally converted for detection by the controller 150. In this manner, by varying the input frequency and/or voltage of the applied input drive signals 131, 132, it is possible to examine the acoustic transmission spectrum of the blood-filled compartment. In one embodiment, the frequency range for stimulating the elements 101, 102 are from between 25 kHz to 1.5 MHz. In one embodiment, a calibration procedure may be implemented prior to operations to establish baseline flow conditions.

Additionally, in a further embodiment shown in FIG. 1, the flow sensor 110 further includes a microphone device 145 which may be additionally embedded on or near an inner or outer surface of the implantable medical device and of sensitivity for real-time capturing the sounds of flowing fluid, e.g., blood, or the sounds of moving valve leaves. In another embodiment, one or more microphones 145 may be embedded for detecting audible acoustic frequency signal(s) in real-time which may be analyzed at the controller 150 to identify laminar versus turbulent flow and/or to acoustically detect opening or closing of the leaves of a prosthetic valve, for example. Detected acoustic signals from at least one microphone 145 may be conducted over conductor 117 for input to another channel at the multichannel amplifier 120 which amplifies the signals and which may be further converted by A/D converter 122 into a digital signal for receipt at the control device 150 for further processing.

In yet another embodiment, the flow sensor 110 further includes at least one pressure sensor 148 which may be additionally embedded on or near an inner or outer surface of the implantable medical device and of sensitivity for monitoring the pressure, e.g., in blood filled compartment 80. Detected signals representing a real-time condition of the blood pressure from a pressure sensor 148 may be conducted over conductor 118 for input to another channel at the multichannel amplifier 120 which amplifies the signals and which may be further converted by A/D converter 122 into a digital signal for receipt at the control device 150 for further processing In one non-limiting example use, by detecting by the processor 150 a change in pressure distal to piezo-element 101, this information may be used to determine whether a change in blood velocity is the result of a change in blood flow driving force, or a change in the effective cross-section of blood filled compartment 80 (e.g., due to narrowing). In one embodiment, this can be determined by measuring the transverse dimension of the vessel based on phase delay and comparing it to baseline values and known elasticity. Multiple pressure sensors 148 may be used to monitor pressure in different points of blood filled compartment 80.

Further, shown as part of system 100 are a power supply unit 140 which provides power via conductive elements (not shown) to respective elements, e.g., amplifiers, converters, microprocessor elements of system 100. A power source unit 140 may comprise a micro-sized battery and/or an ultracapacitor and it may be able to harvest vibration, heat or chemical energy from the environment in the patient's body, e.g., local tissue in the patient, or fluid flow vibrations may charge an ultracapacitor. The sound emitted from the patient's heart may be converted into energy that can be stored for later use as a power source. In a further embodiment, RF energy may be applied from a source external to the patient and may be received by an antenna/receiver device in vivo which receives and stores the received energy in a small storage device, e.g., battery, capacitor, in the implanted device, that can run the device or an amount of time. In particular, an antenna may function to passively receive electrical energy, and couple energy to a rectifier device (not shown) which may rectify the energy signals to obtain power for powering one or more configured components. Thus, module 100 may be powered by induction or RF coupling. In a further embodiment, ultrasound energy transmitted from outside of the body can be used to supply energy needed for the device to function or charge a battery or a microcapacitor.

As power budgets may be small, e.g., in microwatt range, and the use and amount of power sources may vary depending upon the size of the implantable device, the number of piezo-elements, amplifiers, and the controller. Further, the use of the energy may be duty-cycled, e.g., run periodically, and turned on/off periodically depending upon cost constraints, or for lower power budget requirements, may run virtually continuously.

In operation, a reflected acoustic signal is captured by piezo-element 101 and causes voltage to be produced in piezo-element 101 that is sensed using the differential amplifier and A/D converter 120. This sensed signal can be differentially compared to the signal from piezo element 102 by differential amplifier and A/D converter 120.

In one embodiment, the piezo-elements 101, 102 are located diagonally or laterally on the blood vessel such that a change in the pitch of the acoustic signal resulting from the movement of blood cells (i.e., a Doppler shift) in the blood-filled compartment 80 indicates the velocity of flow across that compartment.

In one embodiment, the controller 150 is programmed to obtain data of the observed frequency f and emitted frequency $f_0$ and compute the difference in velocity according to:

$$f = \left(\frac{c + v_r}{c + v_s}\right) f_0$$

where c is the velocity of waves in the medium; $v_r$ is the velocity of the receiver relative to the medium; e.g., positive if the receiver is moving towards the source (and negative in the other direction); $v_s$ is the velocity of the source relative to the medium; positive if the source is moving away from the receiver (and negative in the other direction).

In one non-limiting embodiment, the piezo-elements are located on opposite sides of the blood vessel such that the resonant frequency observed at each element reflects the cross sectional distance across the vessel. Blood vessels are flexible and change size due to flow and pressure in the vessel (e.g. due to heartbeat). Since the cross section area of the blood filled compartment 80 is known (e.g., the diameter of an aortic graft or the open cross sectional area of a prosthetic heart valve), the blood flow rate across it (e.g., liters/minute) can be computationally extracted using the digital microprocessor based device 150 or other remote computing device.

The diameter of a blood vessel can further be measured by the flow monitor system 100. For example, in one embodiment, the diameter of the vessel can be measured by the phase delay of the ultrasound signal received in a transmitter piezo-element 101 relative to the emission signal of a receiver piezo-element 102 as detected by the system. The doppler signal is measured by frequency shift between the emitted signal from transmitter piezo-element 101 and receiver piezo-element 102. To determine the frequency shift one embodiment implements a method to fit a sinusoid to the reference (i.e., emitted signal) and to the observed (i.e., received signal) and makes a comparison to determine relative frequency and phase. An alternative method would be to apply Fourier Transform methods (e.g. a DFT) to determine the frequency, magnitude and phase of each signal.

Thus in the embodiments herein, either piezo-element 101 or 102 may be used as an emitter and/or receiver. In one operational mode, one piezo-element is used to emit a vibrational frequency signal. A second piezo-element located proximate and downstream the first piezo-element is used to receive it. Applying a time varying voltage (e.g., a sinusoid) to a piezo-element causes it to vibrate or emit a signal. If a piezo-element is vibrated, it will develop a voltage proportional to the degree of vibration which proportional voltage can be sensed.

In another operation mode, embedded piezo-elements 101, 102 are located on an opposite an inner surfaces of the compartment or passage and one of them, e.g., element 102 is driven by amplifier/digital to analog converter 115 with a digital signal 152 from computer 150. This causes piezo-element 102 to vibrate and emit a signal. The signal travels across the medium (blood) and causes the piezo-element 101 to vibrate and produce a voltage that is measured and digitized by amplifier/analog to digital converter 120 and relayed to computer 150 for analysis in computing flow.

Figure 2:
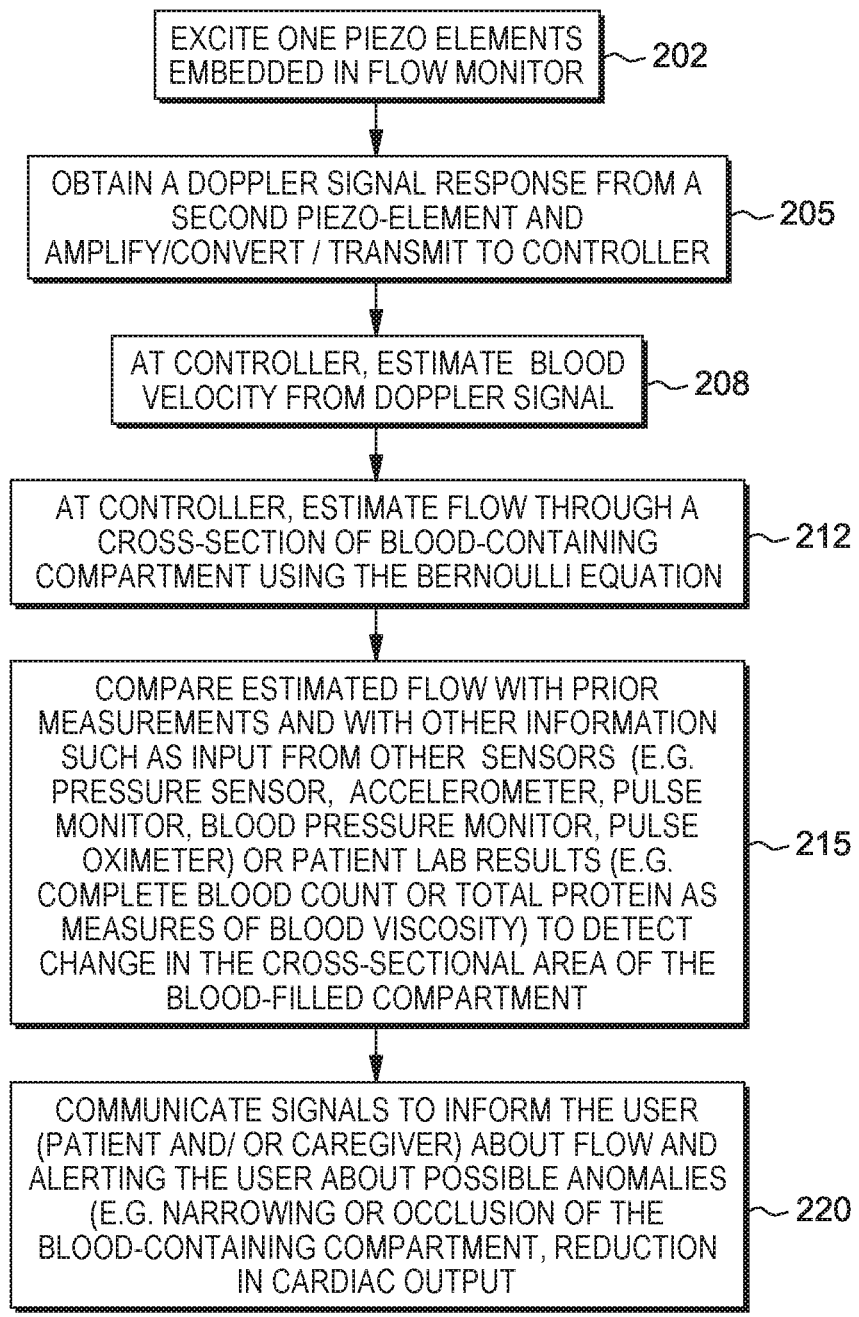
FIG. 2 illustrates a method of operating a flow detection sensor embedded within a prosthetic mitral valve or stent in one embodiment.

FIG. 2 shows an exemplary method 200 of operating flow monitor system 100. Step 202, FIG. 2 depicts a step of ultrasonically exciting one of the piezo-elements, e.g., element 101 for sensing by the second piezo-element 102. In this embodiment, the acoustic signal originating from piezo-element 101 reaches piezo-element 102 across compartment 80 through the fluid medium (blood) and vibrates it, thus causing a voltage to be produced in piezo-element 102. At 205, the Doppler signal response output at piezo-element 102 is amplified and D/A converted for real-time receipt and/or storage at controller device 150.

In FIG. 2, at 208, processing is initiated to estimate the velocity of the fluid, e.g., blood, from the detected Doppler signal. Either during or after the stimulus driving signal is applied to the first piezo-element, the motion (velocity) of the fluid may be estimated based on the differential in sound produced by the energized element. In one embodiment, the estimate is obtained by comparing the difference of the voltage signals received, e.g., comparing in time the waveform of the original stimulus frequency signal against the waveform of the response signal emitted at the second piezo-element at the output of the differential amplifier 120. The comparison is performed digitally at the controller device to detect a frequency or phase shift in the manner as described herein. For example, at 208, the digital controller 150 compares the analog voltage produced at piezo-element 102 output against the input signal voltage used to excite the first piezo-element which signal is captured via input conductor 111A by differential amplifier 120. In one embodiment, the difference between the input excitation and sensor response frequencies indicate the frequency shift which value is received as input to the controller 150 for further processing.

In a further embodiment, at 212, based on the recorded Doppler signal read at the second piezo-element, processing may be further initiated to estimate the amount of blood flow through a cross-section of blood-containing compartment using the known Bernoulli equation. For example, a common form of Bernoulli's equation, valid at any arbitrary point along a streamline, is:

$$\frac{v^2}{2} + gz + \frac{p}{\rho} = \text{constant}$$

where: v is the fluid flow speed at a point on a streamline, g is the acceleration due to gravity, z is the elevation of the point above a reference plane, e.g., with the positive z-direction pointing upward—so in the direction opposite to the gravitational acceleration, p is the pressure at the chosen point, and $\rho$ is the density of the fluid at all points in the fluid.

In a further embodiment, in FIG. 2, at 215, based on the recorded Doppler signal read at the second piezo-element, and further based on received extraneous signals from other sensor devices monitoring physical activities in the body, processing may be further initiated to detect a change in a cross-sectional area of the blood-filled compartment 80. The Bournelli equation may be used above, and with the assumption of incompressible flow, a change in lateral dimension of the vessel may be solved.

The extra signals processed to aid in the detecting a change in a cross-sectional area of the blood-filled compartment may include measurements from a variety of sensor devices including, but not limited to, one or more of: pressure sensor 148, an accelerometer for sensing a dilatation and recoil of a blood vessel associated with heart beats, a pulse monitor, a blood pressure monitor, a pulse oximeter.

Additionally obtained information, e.g., data such as patient lab results (e.g. complete blood count or total protein as measures of blood viscosity) may be used in determining any change in the cross-sectional area. For example, by measuring the pressure gradient across the device, using the pressure sensors, changes in the cross-sectional diameter through which blood flows is detected. That is, a pressure change may result from narrowing of the effective diameter of the blood filled compartment or by increased impedance to flow caused by increased blood viscosity.

Figure 5:
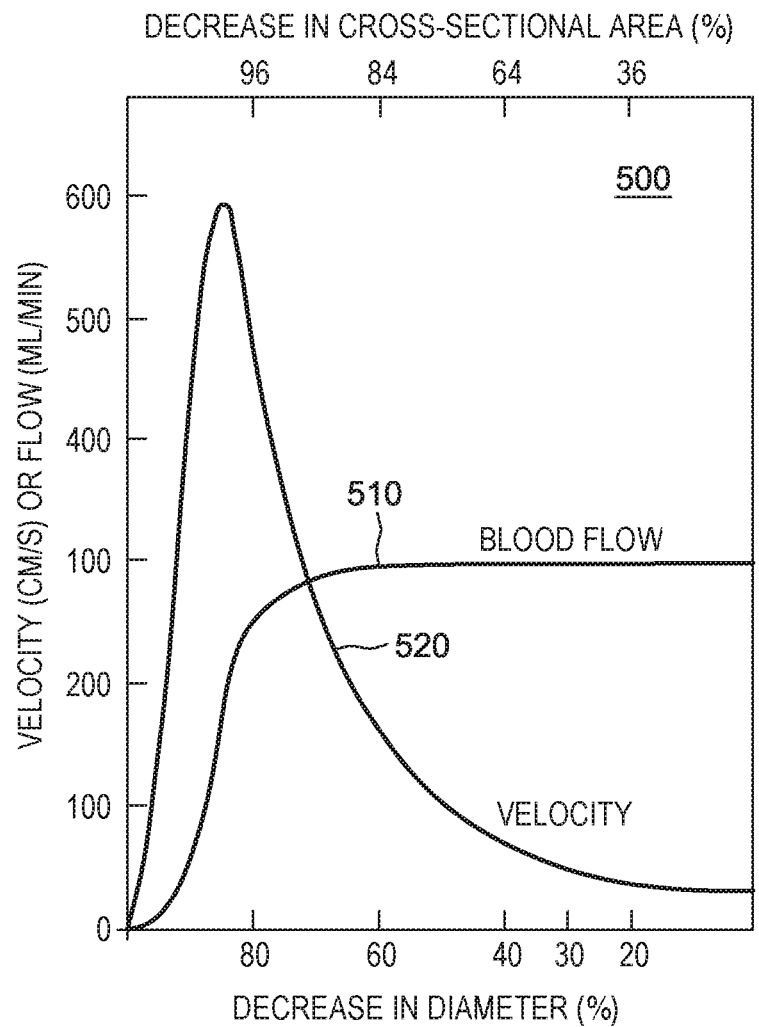
FIG. 5 depicts a graph illustrating how blood flow and velocity measured across a vessel cross sectional area can be used to estimate flow volume when the baseline diameter is known.

FIG. 5 shows a graph 500 depicting an example relationship between flow velocity and lumen size, and in particular graphic depicting a change in blood flow and velocity vs. a change in lumen size. The flow velocity is shown as an indirect measure of the diameter of the blood-filled compartment. The controller device may be programmed with the content of FIG. 5 as a reference. In graph 500, the x-axis represents the decrease in stent or valve diameter (at the bottom as a percentage) or alternatively, represents the decrease in cross-sectional area (on top). Two plots are shown along the y-axis, a first plot 510 showing the velocity change in flow (in volume of liquid/per unit time) as a function of decreasing diameter and plot 520 shows the change of speed (of the flow) as a function of decreasing diameter of the compartment or lumen. Knowing the cross-section area of the lumen, the flow rate can be extrapolated from the detected velocity, and thus the cardiac output may be inferred. For example, the controller 150 may detect a change in velocity as due to increased flow or a reduction in the open cross-sectional area of the lumen. By monitoring the Doppler signal over time, the controller differentiates between a condition of an increase of flow as driving an increase in velocity, or a condition of a reduced cross-sectional area which drives the same increase in velocity. By analyzing the dynamics of the change, it can be inferred what causes the change in the liquid velocity. For example, a constriction developing in the blood-filled compartment, may result in a higher velocity detected; however increased cardiac activity resulting from doing exercise, may also cause the same increase in velocity and not as result of a cross-sectional area change of the blood-filled compartment. Thus, there may be obtained additional available information from patient activities, e.g., a detected increase in heart rate by a pulse monitor, or increased accelerometer sensor output indicating exercise activity the patient undergoes in real-time. Readings from devices located in other parts of the subject's body can be used for reference, as a concurrent increase in flow velocity occurring in two or more locations is suggestive of increased cardiac output rather than lumen narrowing. A monitoring station may correlate the detected changes in the flow with the obtained additional information to pinpoint a particular issue with the patient's organ. This may be determined locally at controller 150, however can be improved and expanded upon by remote processing by an external system, e.g., remote mobile smartphone, computer device or any designated device for processing thereat.

Returning to FIG. 2, at 220, the controller 150 may then initiate the transmission system 160 to wirelessly transmit the data signals 156 representing the monitored blood flow velocity and/or change in cross-sectional area of the compartment organ being monitored, out of the patient's body to a further monitoring device that may record the transmitted signals for further processing. In one embodiment, in particular, the transmitted signals may be received to inform the user (e.g., patient and/or caregiver) about flow and alerting the user about possible anomalies, including, but not limited to: a narrowing or occlusion of the blood-containing compartment, or reduction in cardiac output.

Figure 3:
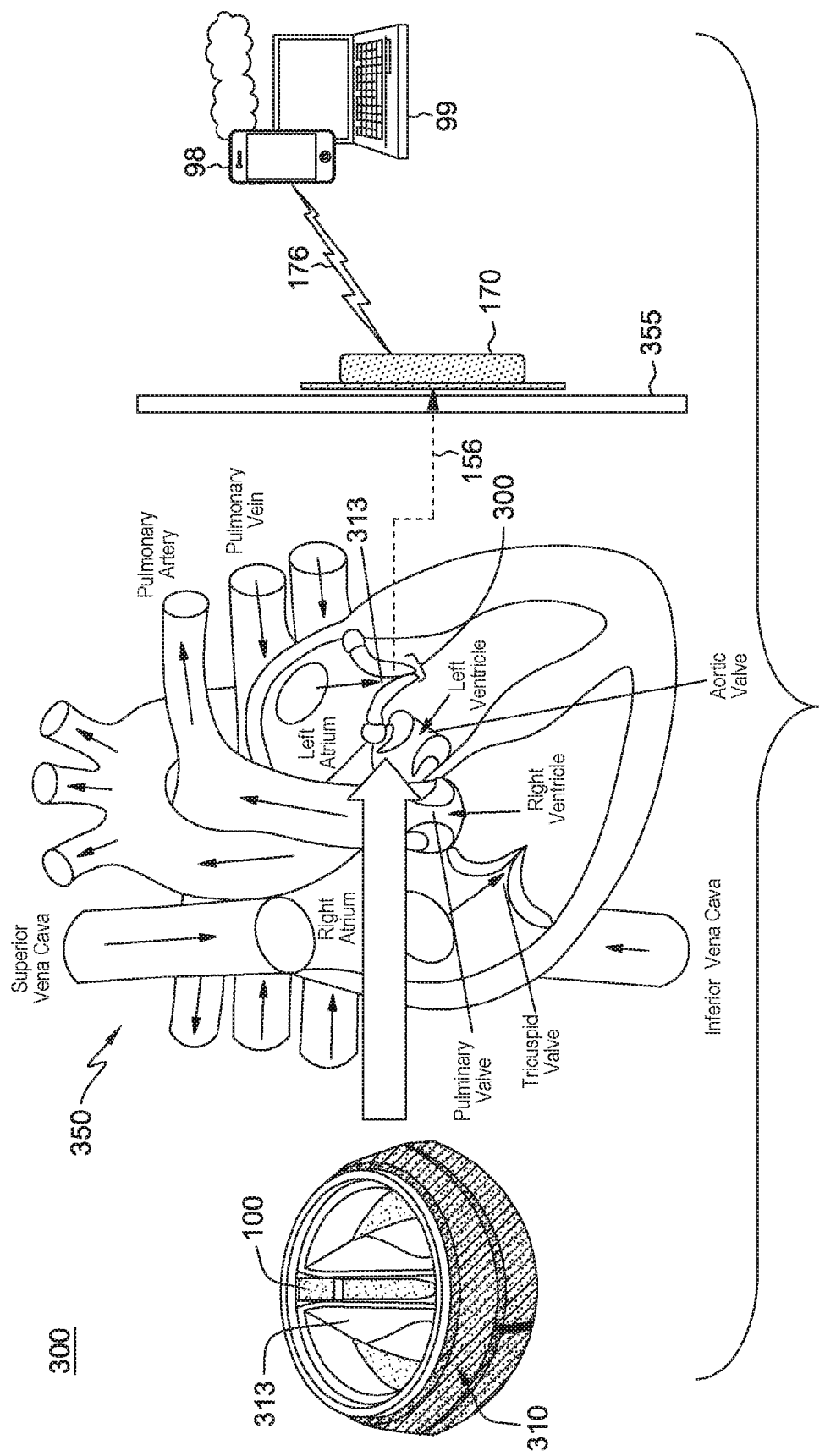
FIG. 3 illustrates an embodiment in which a continuous flow monitor is embedded in a prosthetic heart valve annulus.

FIG. 3 shows an example implementation of the flow monitoring system 100 embedded in a replacement heart valve (i.e., a prosthetic mitral valve) 300 to be inserted for operation within an individual's heart 350. In FIG. 3, the prosthetic mitral valve 300 includes an annulus 310 and twin mitral valve leaves 313. Embedded between the two prosthetic mitral valve leaves 313 is the flow monitoring system 100. In FIG. 3, the prosthetic mitral valve 310 having leaves 313 with embedded flow monitor 100 is depicted for use as a heart valve within a patient's heart 350. In the embodiment depicted, a transceiver, e.g., a receiver device and the transmitter device 160, may be located outside the body of the patient or subject, e.g., located at or on the patient's skin 355 in proximity to the prosthetic mitral valve which may receive signals 156 from the transponder 160 via a wired or wireless communications link. The signals 156 used to monitor the fluid velocity and/or compartment cross-sectional area change may be further transmitted directly from ex-vivo transmitter/receiver 170 as corresponding signals 176 for receipt at a remote monitoring device, e.g., a local mobile smart phone 98, computer 99 or cloud service.

In one embodiment, cardiac output can be accurately measured continuously using flow velocity, relying on the fact that the valve annulus (ring) diameter is known and that the effective cross sectional area (related to valve leaf position throughout the heart cycle) can be computed for all stages of the heart cycle (e.g., using an EKG stream). In one embodiment, an ultrasound receiver and transmitter 170 is positioned in contact with the patient skin and is used to supply energy to the flow monitor 100. In this embodiment, flow monitor 100 is equipped with an ultrasound transponder and an ultracapacitor. Flow monitor 100 uses the transponder 160 to transmit collected information to the receiver and transmitter 170. Receiver and transmitter 170 transmits the information collected by flow monitor 100 as signals 176 to a remote device where it can be further analyzed and compared to other data streams, the patient's EKG signal.

The velocity of blood flow through the mitral valve annulus over time reflects the cardiac cycle stages. A change in the pattern of flow such as increased velocity suggests a narrowing of the effective area through which blood flows. Such change can also be caused by changes in blood volume, heart contractility and relaxation or valve function.

Figure 4:
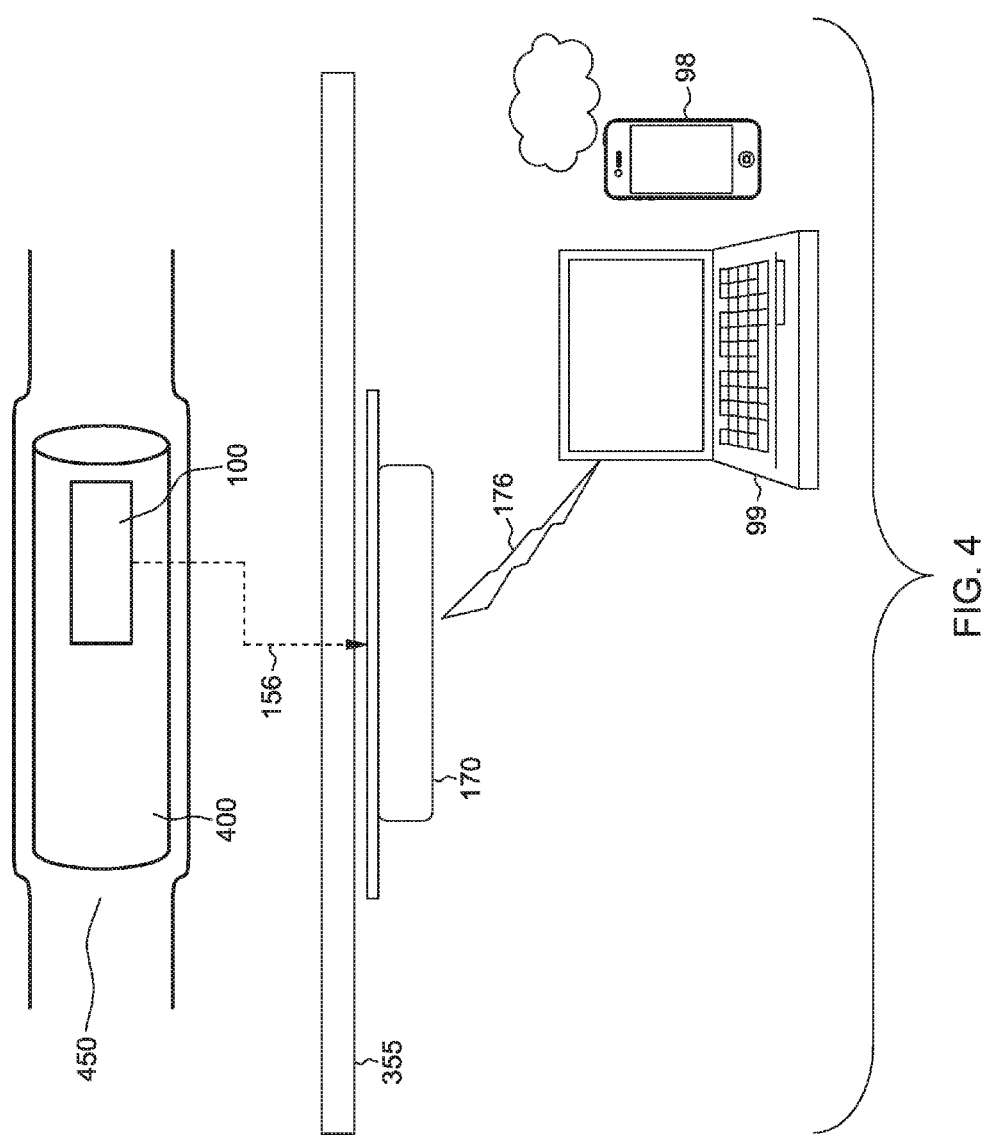
FIG. 4 shows an example implementation of the continuous flow monitoring system 100 embedded in a coronary artery stent.

FIG. 4 shows an example implementation of the continuous flow monitoring system 100 embedded in a coronary artery stent 400 to be implanted in the lumen of a coronary artery or vein within an individual's body. In FIG. 4, the coronary stent 400 is a mesh tube or similar tubular structure creating a passage between two spaces on either side of the stent within which blood flows. Embedded on an inner surface of the tubular stent 400 is the flow monitoring system 100. In FIG. 4, the coronary artery stent 400 with embedded flow monitor 100 is depicted for use within an artery (or vein) within a patient's body. In the embodiment depicted, the transceiver 170 located ex-vivo (outside the body of the patient such as at or on the patient's skin 355) in proximity to the stent 400 which may receive signals 156 from the transponder 160 via the wired or wireless communications link 156. The signals 156 used to monitor the fluid velocity and/or compartment cross-sectional area change of the artery may be transmitted directly from ex-vivo transmitter 170 to a remote monitoring device, e.g., a local mobile smart phone 98, a smart watch, a laptop computer 99 or cloud service, such as to inform the patient and others (e.g. medical caregiver) of a detected condition.

In the embodiment of FIG. 4, a continuous flow monitor 100 is embedded in a coronary artery stent, implanted in the lumen of a coronary artery, the flow monitor uses the transponder to transmit collected information to the receiver and transmitter. Receiver and transmitter 105 can transmit the information collected by flow monitor 101 to a remote device 106 (e.g. a smartphone, computer or cloud service) where it can be further analyzed and compared to other data streams such as EKG. A change in the pattern of flow such as increased velocity may suggest narrowing of the effective area through which blood flows. Occlusion of the stent (e.g. by a thrombus, an embolus, a plaque or restenosis) will result in reduced flow velocity across the stent. Any detected changes in blood flow may be coupled with additional information to determine, at a remote monitoring device, existence of a pathologic process such as thrombus formation, embolus localization, aneurysm, arterio-venous malformation, vessel narrowing, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the application has been described in terms of specific embodiments, it is evident in view of the foregoing description that numerous alternatives, modifications and variations will be apparent to those skilled in the art. Each of the embodiments described herein can be implemented individually or in combination with any other embodiment unless expressly stated otherwise or clearly incompatible. Accordingly, the application is intended to encompass all such alternatives, modifications and variations which fall within the scope and spirit of the application and the following claims.

What is claimed is:

1. A system for monitoring a health status of a subject comprising:
    a prosthetic cardiac valve implantable in the subject's heart and having an annulus body defining a compartment through which blood flows through upon an opening of cardiac valve leaves;
    a first piezo-electric element embedded within said annulus body at or near a surface of said annulus body for generating acoustic excitation signals that traverse a liquid blood medium within said compartment, and one or more second piezo-electric elements embedded within said annulus body and configured to receive said acoustic excitation signal and responsively generating an output signal for measuring a Doppler shift effect occurring within said compartment;
    a signal generator for applying a stimulus signal to said first piezo-electric element for generating an acoustic excitation signal;
    a multichannel amplifier configured for receiving a signal output from the one or more second piezo-electric elements in response to receiving said acoustic excitation signal, and comparing, in real time, a generated output signal with the excitation signal to output a Doppler frequency shift measurement signal; and
    an A/D converter for receiving a frequency shift measurement output signal from said amplifier and converting said frequency shift measurement output signal to a corresponding digital signal,
    a microphone sensor embedded on an outer surface of the implanted prosthetic cardiac valve for real-time capturing of sound of blood flowing through said cardiac valve leaves opening and generating corresponding data signals of said captured sounds;

a processor element coupled to said multichannel amplifier for receiving said corresponding digital signal for use in real time measuring the liquid blood flow rate across said compartment, and monitoring a cardiac output and a function of the prosthetic cardiac valve based on said received digital signal, said processor element further configured to identify a laminar blood flow versus a turbulent blood flow based on said captured sounds, and correlate said generated data signals received from said embedded microphone sensor with the corresponding digital signal to identify a change in said cardiac output.

2. The system of claim 1, further comprising:

a communications transceiver for transmitting signals to and receiving signals from a device external to said subject, said external device comprising a mobile phone, a smartphone, a laptop, a computer device configured for operator-independent, continuous monitoring of blood flow rate and/or measurement of cardiac output.

3. The system of claim 2, wherein said processor element is further configured to: determine, in real-time, whether a change in monitored liquid blood flow velocity is a result of a change in the cross-sectional area of the compartment or a change in the blood flow rate.

4. The system of claim 3, wherein said processor element is configured to analyze received embedded piezo-electric sensor data, said processor element is further configured to:
correlate data signals received from one or more other sensor devices with received sensor generated output signals, said correlating used for determining whether a detected change in blood flow rate results from a change in the cross-sectional area of the compartment or the change in cardiac output.

5. The system of claim 4, wherein said other sensor devices providing data signals for correlation comprise one or more of: a pressure sensor device, a pulse monitor device, an accelerometer device for sensing dilatation and recoil of a blood vessel associated with a heartbeat, or an EKG (electrocardiogram) signal.

6. The system of claim 3, wherein said communications transceiver transmit signals to said mobile phone, smartphone, laptop, or computer device configured to analyze received embedded piezo-electric sensor data, and further configured to correlate data signals received from one or more other sensor devices for determining whether a detected change in blood flow rate results from a change in the cross-sectional area of the compartment or the change in cardiac output.

7. The system of claim 2, further comprising an ultracapacitor for harvesting energy generated in the body of the user, said ultracapacitor providing energy for operating said embedded piezo-electric elements sensor and communication tranceiver, said ultracapacitor harvesting energy converted from one of: fluid flow vibration, heat, or sound produced from local tissue in the subject.

8. A method for monitoring a health status of a subject comprising:
applying, using a signal generator, a stimulus signal to a first piezo-electric element embedded within an annulus body of a prosthetic cardiac valve at or near a surface of said annulus body, the prosthetic cardiac valve implanted in the subject's heart, the annulus body defining a compartment through which blood flows through upon an opening of cardiac valve leaves, said first embedded piezo-electric element configured to generate acoustic excitation signals that traverse a liquid blood medium within said compartment, said prosthetic cardiac valve having one or more second piezo-electric elements embedded at or near a surface of said annulus body and configured to receive said acoustic excitation signals;

generating acoustic excitation signals, by said embedded first piezo-electric element, said acoustic excitation signals traversing a liquid blood medium within said compartment for receipt at said second piezo-electric element embedded within the annulus body, said second piezo-electric element responsively generating an output signal for measuring a Doppler shift effect occurring within said compartment;

receiving, at a multichannel amplifier, a signal output from the one or more second piezo-electric elements in response to receiving said acoustic excitation signal, comparing, in real time, a generated output signal with the excitation signal to output a Doppler frequency shift measurement signal;

receiving, at an A/D converter element, the frequency shift measurement output signal from said amplifier and converting said frequency shift measurement output signal to a corresponding digital signal, real-time capturing, using a microphone sensor embedded on an outer surface of the implanted prosthetic cardiac valve of sound of blood flowing through said cardiac valve leaves opening and generating corresponding data signals of said captured sounds;

communicating said corresponding digital signal to a processor element; and determining at said processor element, a real time liquid blood flow rate measure within said compartment based on said received corresponding digital signal for use in real time monitoring a cardiac output and a function of the prosthetic cardiac valve, and using said processor element to identify a laminar blood flow versus a turbulent blood flow based on said captured sounds, and correlate said generated data signals received from said embedded microphone sensor with the corresponding digital signal to identify a change in said cardiac output.

9. The method of claim 8, further comprising:

transmitting, via a communications transceiver, signals representing said determined liquid blood flow rate measure to a processor device external to said subject, said external processor device comprising a mobile phone, a smartphone, a laptop, or a computer device configured for operator-independent, continuous monitoring of blood flow rate and/or measurement of cardiac output.

10. The method of claim 9, further comprising:

determining, in real time, at said processor element, whether a change in monitored liquid blood flow velocity is a result of a change in the cross-sectional area of the compartment or a change in the blood flow rate.

11. The method of claim 10, wherein said processor element is configured to analyze received embedded piezo-electric sensor data, said method further comprising:

correlating data signals received from one or more other sensor devices with received sensor generated output signals at said processor device, said correlating used for determining whether a detected change in blood flow rate results from a change in the cross-sectional area of the compartment or a change in cardiac output.

12. The method of claim 11, wherein said other sensor devices providing data signals for correlation comprise one or more of: a pressure sensor device, a pulse monitor device, an accelerometer device for sensing dilatation and recoil of a blood vessel associated with a heartbeat, or an EKG (electrocardiogram) signal.

13. A computer program product comprising:
a computer readable storage device, tangibly embodying a program of instructions executable by a computing device for monitoring a health status of a subject, said subject having a prosthetic cardiac valve implanted in the subject having an annulus body defining a compartment through which blood flows through upon an opening of cardiac valve leaves, said prosthetic cardiac valve having a first piezo-electric element embedded within said annulus body at or near a surface of said annulus body and configured to generate acoustic excitation signals that traverse a liquid blood medium within said compartment and having one or more second piezo-electric elements embedded within the annulus body at or near a surface of said annulus body within said prosthetic cardiac valve and configured to receive said acoustic excitation signals, said program of instructions configuring a processor element to:
apply, using a signal generator, a stimulus signal to the embedded first piezo-electric element for generating an acoustic excitation signal;
receive, at a multichannel amplifier, a signal output from the one or more second piezo-electric elements in response to receiving said acoustic excitation signal,
compare, in real time, a generated output signal with the excitation signal to output a Doppler frequency shift measurement signal;
receive, at an A/D converter element, the frequency shift measurement output signal from said amplifier and converting said frequency shift measurement output signal to a corresponding digital signal,
receive said corresponding digital signal at said processor element; and
capture, in real-time, using a microphone sensor embedded on an outer surface of the implanted prosthetic cardiac valve, a sound of blood flowing through said cardiac valve leaves opening and generate corresponding data signals of said captured sounds;
determine at said processor element, a real time liquid blood flow rate measure within said compartment based on said received corresponding digital signal for use in real time monitoring a cardiac output and a function of the prosthetic cardiac valve, and
identify, at said processor element, a laminar blood flow versus a turbulent blood flow based on said captured sounds, and correlate said generated data signals received from said embedded microphone sensor with the corresponding digital signal to identify a change in said cardiac output.

14. The computer program product of claim 13, said program of instructions configuring said computing device to initiate a communications transceiver to:
transmit signals representing said determined liquid blood flow rate measure to a device external to said subject, said external device comprising a mobile phone, a smartphone, a laptop, a computer device configured for operator-independent, continuous monitoring of blood flow rate and/or measurement of said cardiac output.

15. The computer program product of claim 14, wherein said program of instructions further configure the processor element to:
determine, in real time, whether a change in monitored liquid blood flow velocity is a result of a change in the cross-sectional area of the compartment or a change in the blood flow rate.

16. The computer program product of claim 15, wherein said program of instructions further configure the processor element to:
analyze received embedded piezo-electric sensor data; and
correlate data signals received from one or more other sensor devices with received sensor generated output signals at said processor device, said correlating used for determining whether a detected change in blood flow rate results from a change in the cross-sectional area of the compartment or a change in said cardiac output.

17. The system of claim 3, wherein a change in a cross-sectional area of the compartment is a function of a cardiac valve leaves position throughout a human heart cycle, said processor element monitoring said liquid blood flow velocity for all stages of the heart cycle.

18. The method of claim 10, wherein a change in a cross-sectional area of the compartment is a function of a cardiac valve leaves position throughout a human heart cycle, said processor element monitoring said liquid blood flow velocity for all stages of the heart cycle.

19. The computer program product of claim 15, wherein a change in a cross-sectional area of the compartment is a function of a cardiac valve leaves position throughout a human heart cycle, said processor element monitoring said liquid blood flow velocity for all stages of the heart cycle.

20. The method of claim 9, further comprising:
using an ultracapacitor to harvest energy generated in the body of the user, said ultracapacitor harvesting energy converted from one of: fluid flow vibration, heat, or sound produced from local tissue in the subject, and said ultracapacitor providing energy for operating said embedded piezo-electric elements sensor and communication tranceiver.

* * * * *